United States Patent
Bieri et al.

(10) Patent No.: US 10,517,509 B2
(45) Date of Patent: Dec. 31, 2019

(54) ASSESSMENT OF THE LUNG PARENCHYMA BY MEANS OF MAGNETIC RESONANCE IMAGES

(71) Applicant: UNIVERSITÄTSSPITAL BASEL, Basel (CH)

(72) Inventors: Oliver Bieri, Liestal (CH); Orso Andrea Pusterla, Ligornetto (CH); Grzegorz Bauman, Basel (CH)

(73) Assignee: UNIVERSITATSSPITAL BASEL, Basel (CH)

( * ) Notice: Subject to any disclaimer, the term of this patent is extended or adjusted under 35 U.S.C. 154(b) by 721 days.

(21) Appl. No.: 15/251,285

(22) Filed: Aug. 30, 2016

(65) Prior Publication Data

US 2018/0055414 A1 Mar. 1, 2018

(51) Int. Cl.
*A61B 5/055* (2006.01)
*A61B 5/091* (2006.01)
*G01R 33/56* (2006.01)

(52) U.S. Cl.
CPC .............. *A61B 5/091* (2013.01); *A61B 5/055* (2013.01); *G01R 33/5608* (2013.01)

(58) Field of Classification Search
None
See application file for complete search history.

(56) References Cited

U.S. PATENT DOCUMENTS

| 2010/0324409 | A1* | 12/2010 | Assmann | A61B 5/055 600/410 |
| 2011/0009731 | A1* | 1/2011 | Damadian | A61B 5/055 600/410 |

OTHER PUBLICATIONS

Brett A. Simon, MD., Ph.D, "Non-Invasive Imaging of Regional Lung Function Using X-Ray Computed Tomography", Journal of Clinical Monitoring and Computing, 2000, pp. 433-442, vol. 16.
Thomas Guerrero, et al., "Dynamic ventilation imaging from four-dimensional computed tomography", Physics in Medicine and Biology, 2006, pp. 771-791, vol. 51.
(Continued)

*Primary Examiner* — Jonathan Cwern
(74) *Attorney, Agent, or Firm* — Sughrue Mion, PLLC (57) ABSTRACT

A method for the assessment of the lung parenchyma in a human or an animal is indicated using a series of magnetic resonance (MR) images of the lung parenchyma acquired at different breathing positions in the same human or animal. The method comprises at least the steps of a.) estimating a change of the lung volume $V_L$ between the different breathing positions, b.) determining a signal intensity $SI(\vec{x}_i)$ in at least one same region or position $\vec{x}_i$ of the lung parenchyma for each of the MR images, and c.) determining at least one respiratory index $\alpha(\vec{x}_i)$ according to the formula $$\alpha(\vec{x}_i) = -\frac{d(\log(SI(\vec{x}_i)))}{d(\log(V_L))}.$$ (Fig. 2)

19 Claims, 6 Drawing Sheets

(56) References Cited

OTHER PUBLICATIONS

M. Staring, et al., "Towards Local Estimation of Emphysema Progession Using Image Registration", Proc SPIE, 2009, 72590O-72590O-9.

Oliver Bieri, "Ultra-Fast Steady State Free Precession and Its Application to In Vivo 1H Morphological and Functional Lung Imaging at 1.5 Tesla", Magnetic Resonance in Medicine, 2013, pp. 657-663, vol. 70.

Orso Pusterla, et al., "How volume affects the pulmonary MRI signal: Investigations with 3D ultra-fast balanced Steady-State Free Precession", Proc. Intl. Soc. Mag. Reson. Med., 2015, p. 1481, vol. 23.

Grzegorz Bauman, et al., "Non-Contrast-Enhanced Perfusion and Ventilation Assessment of the Human Lung by Means of Fourier Decomposition in Proton MRI", Magnetic Resonance in Medicine, 2009, pp. 656-664, vol. 62.

* cited by examiner

ASSESSMENT OF THE LUNG PARENCHYMA BY MEANS OF MAGNETIC RESONANCE IMAGES

TECHNICHAL FIELD

The present invention concerns a method for the assessment of the lung parenchyma in a human or an animal using magnetic resonance (MR) images. The present invention also concerns a computer program comprising executable instructions for the assessment of the lung parenchyma in a human or an animal by means of MR images as well as a MR imaging system configured for acquiring MR images of a human or an animal lung and for assessing the lung parenchyma based on these images.

PRIOR ART

Periodical bidirectional airflow is the primary process taking place in the lung, enabling gas exchange in the alveoli. As a result, the measurement of both, global and local lung ventilation is a key parameter not only to diagnose and understand pathophysiology in lung diseases, but also for monitoring the progression and the response to therapeutic procedures.

A global measure of lung ventilation can be obtained by conventional whole-lung spirometry, plethysmography or multiple-breath washout tests. These conventional pulmonary function tests, however, fail to provide information about regional lung processes which can provide fundamental insights into pathophysiologic mechanisms or improve therapies by a tailoring for specific lung regions and disease phenotypes.

A broad spectrum of imaging modalities is available to assess the regional lung ventilation. Single-photon emission computed tomography (SPECT), planar scintigraphy and positron emission tomography (PET) are nuclear medicine imaging modalities based on radioactive labeled tracer administration. Despite their relatively poor spatial and temporal resolution, SPECT and PET are commonly used in the clinical routine for lung functional imaging. High spatial resolution ventilation imaging in short scanning times is possible by means of dynamic contrast-enhanced computed tomography (CT).

CT-methods do derive ventilation-related information based on two-dimensional (2D) images and models tailored for CT are presented by Simon B A: Non-Invasive Imaging of Regional Lung Function using X-Ray Computed Tomography. J Clin Monit 2000; 16: 433-442 and by Guerrero T, Sanders K, Castillo E, Zhang Y, Bidaut L, Pan T, Komaki R: Dynamic ventilation imaging from four-dimensional computed tomography. Phys. Med. Biol. 51 (2006) 777-791. These models, when further modified, can be used to derive a measure of the lung emphysema progression thanks to a density-volume slope model (sponge model) between baseline and follow-up examinations, as presented by Staring M, Bakker M E, Shamonin D P, Stolk J, Reiber J H C, Stoel B C: Towards local estimation of emphysema progression using image registration. Proc SPIE 2009:72590O-72590O-9. A density-volume slope model (sponge model) for CT is proposed in this document to correct for the different inspiratory volumes between baseline and follow-up examinations, which would flaw the emphysema progression measurement.

Despite the constant progress of nuclear medicine and CT in reducing radiation doses, exposure to any ionizing radiation is still of concern, especially for children, pregnant women, or patients who require frequent follow-up examinations.

Alternatively, magnetic resonance imaging (MRI) is an attractive radiation-free imaging modality, and over the last decade a variety of powerful methods have been developed for the evaluation of both lung morphology and function. Among them, non-proton based lung imaging with hyperpolarized noble gases, such as Helium-3 or Xenon-129, has demonstrated the ability to measure various pulmonary functional biomarkers; furthermore, the pulmonary ventilation can also be visualized in MRI using inert fluorinated gas tracers which has shown lately high quality images similar to those from hyperpolarized gases. Gas ventilation MRI, however, is limited to few specialized medical centers, mainly due to high cost, complexity and requirements for experimental hardware.

In contrast, non-invasive, proton-based, imaging of regional lung function is possible in vivo using a technique known as Fourier decomposition (FD) MRI (Bauman G, Puderbach M, Deimling M, et al.:Non-contrast-enhanced perfusion and ventilation assessment of the human lung by means of Fourier decomposition in proton MRI. Magn Reson Med 2009; 62:656-664). This approach utilizes dynamic balanced steady state free precession (SSFP) imaging in free-breathing with subsequent image registration and voxel-wise spectral analysis to extract local ventilation and perfusion information. FD MRI is based on native balanced SSFP imaging, thus requires no administration of contrast agent, but from the required time-resolution to separate perfusion from ventilation, FD MRI is a single slice method. As a result, a stack of coronal 2D slices needs to be acquired to cover the whole lung volume, thus proffering relatively low through plane resolution.

By means of a MRI method referred to as 3D ultra-fast balanced SSFP (ufSSFP), it is possible to acquire three-dimensional (3D), i.e. volumetric chest scans of the lung at different inspiratory volumes (multi-volume 3D MRI) (Bieri O: Ultra-fast steady state free precession and its application to in vivo 1H morphological and functional lung imaging at 1.5 tesla. Magn Reson Med 2013; 70:657-663).

It could be shown, that 3D ufSSFP is sensitive to depict the signal intensity modulations of the lung parenchyma arising by diverse inspiratory levels (Pusterla O, Bauman G, Bieri O: How volume affects the pulmonary MRI signal: Investigations with 3D ultra-fast balanced Steady-State Free Precession. Edited by Proc. Intl. Soc. Mag. Reson. Med. 23, 2015:1481). In the method introduced by this document, the lung parenchyma is mechanically considered as a sponge-like tissue, which periodically expands and contracts following the movement of the diaphragm and chest walls, resulting in bidirectional air-flow and ventilation.

SUMMARY OF THE INVENTION

It is an object of the present invention to provide a proton-based and contrast-agent-free MRI method which provides reliable regional information related to pulmonary respiration. The method should be applicable in the clinical setting and particularly also in patients with shortness of breath and cooperative children.

In order to achieve this object, the present invention provides a method for the assessment of the lung parenchyma in a human or an animal using a series of magnetic resonance (MR) images, in particular of 3D MR images, of the lung parenchyma acquired at different breathing positions (thus 4D-MRI in case of 3D MR images) in the same human or animal, comprising at least the following steps:
a.) estimation of a change of the lung volume $V_L$ (the whole lung volume or a portion of the whole lung volume) between the different breathing positions;
b.) determination of a signal intensity $SI(\vec{x}_i)$ in at least one same region or position $\vec{x}_i$ of the lung parenchyma for each of the MR images; and
c.) determination of at least one respiratory index $\alpha(\vec{x}_i)$ according to the formula $$\alpha(\vec{x}_i) = -\frac{d(\log(SI(\vec{x}_i)))}{d(\log(V_L))}.$$

Basically, the lung parenchyma can mechanically be considered as a sponge-like tissue, which periodically expands and contracts thanks to the movement of the diaphragm and chest walls, thus allowing bidirectional airflow and ventilation. In a simple dry sponge model where the sponge mass is constant, the signal intensity of MR images acquired for example by 3D ufSSFP is inversely proportional to the lung volume $V_L$:

$$SI(V_L) = \frac{\Lambda}{V_L} + \eta,$$

where $\Lambda$ is a signal intensity scaling factor (parenchymal mass), and $\eta$ is the SI in the limit of infinite volume, i.e. noise. The assumption of mass preservation in the dry sponge model, however, is not precise enough to model the lung mechanics due to physiological changes such as the blood volume variability during breathing and in presence of ventilation inhomogeneities or regional abnormalities. As a result, the equation of the dry sponge model needs to be modified to take the following form of the adapted sponge model:

$$SI(V_L) = \Lambda^* V_L^{-\alpha} + \eta,$$

where $\alpha$ is referred to as the respiratory index, which maps lung expansion and changes in pulmonary blood volume during breathing. On a logarithmic scale, the adapted sponge model yields $$\log(SI) = \log(\Lambda^* V_L^{-\alpha} + \eta) \approx \log(\Lambda^* V_L^{-\alpha}) = \log(\Lambda) - \alpha^* \log(V_L),$$

where $\eta \ll \Lambda^* V_L^{-\alpha}$ is assumed, and $\alpha$ can be estimated globally (considering the mean SI over the whole lung volume, $SI_{global}$) using $$\alpha_{global} = -\frac{d(\log(SI_{global}))}{d(\log(V_L))}.$$

Similarly, after spatially matching the lung structures of the multi-volume acquisitions, for example by a deformable registration algorithm, the respiratory index can be estimated locally at the position(s) $\vec{x}_i$ (e.g. voxel wise), in order to yield the formula according to step c.):

$$\alpha(\vec{x}_i) = -\frac{d(\log(SI(\vec{x}_i)))}{d(\log(V_L))}.$$

The global respiratory index $\alpha_{global}$ is a measure for blood mass change during the respiratory cycle, as a function of the total lung volume:
$\alpha_{global} = 1$: no mass is leaving nor entering the system, and the dry sponge model is satisfied.
$\alpha_{global} > 1$: blood leaves the lung and its density decreases faster than in the dry sponge model.
$\alpha_{global} < 1$: blood enters the lung and its density decreases slower than in the dry sponge model.

The local respiratory index $\alpha(\vec{x}_i)$ is a measure for the local change of the SI (e.g. in a certain lung region or position, such as in a voxel) over the respiratory cycle, as a function of the total lung volume:
For $\alpha(\vec{x}_i) = 1$, the SI decrease is as in the dry sponge model: The voxel expansion is proportional to the lung-average expansion and no blood is entering or leaving the voxel or the voxels of the respective region or position $\vec{x}_i$.
For $\alpha(\vec{x}_i) < 1$ during inspiration, the SI of the respective region or position $\vec{x}_i$ decreases slower than can be contributed to the increase of the total lung volume, meaning that pulmonary blood is entering the system or a region with a reduced local ventilation which expands at a rate lower than the entire lung-average is present.
For $\alpha(\vec{x}_i) > 1$ the opposite is taking place: Blood is leaving or there is overextended ventilation in the respective region or position $\vec{x}_i$ (the expansion rate is higher than the entire lung average expansion).

Thus, the local respiratory index $\alpha(\vec{x}_i)$ as determined in step c.) represents a regional isotropic three-dimensional (3D) measure that directly relates to the local pulmonary function.

Thus, MR images that have been acquired beforehand, i.e. before step b.), usually also before step a.), are used to determine at least one respiratory index $\alpha(\vec{x}_i)$. The acquisition of the MR images can constitute a further step a0.) of the method. The series of MR images comprises at least two images or preferably more, at least five, more preferably at least nine MR images, and most preferably at least 13 MR images, of the lung parenchyma which are each acquired at a different breathing position of the same human or animal.

In step a0.), the series of MR images is preferably acquired by means of a balanced steady state free precession (SSFP) imaging sequence, in particular a 3D ufSSFP sequence as disclosed in Bieri O: Ultra-fast steady state free precession and its application to in vivo 1H morphological and functional lung imaging at 1.5 tesla. Magn Reson Med 2013; 70:657-663, the disclosure of which is hereby incorporated by reference. A good through plane resolution can be achieved by applying a 3D data acquisition sequence. Indubitably other pulse sequences, e.g. GRE, UTE, ZTE, in 2D or more space-time dimensions can be used as imaging technique.

For acquiring the MR images, a commercial MRI whole-bode scanner is usually used preferably having a main magnetic field of 1.5 T. Of course, it is also possible to acquire the MR images on a 3 T scanner or on a MR scanner having a smaller or a higher main magnetic field.

Step a.) can be carried out before step b.), after step b.) or together with step b.). Step c.) is usually carried out after completion of both of steps a.) and b.).

For the determination of the signal intensities $SI(\vec{x}_i)$ in step b.), usually signal magnitudes are identified in the MR images at certain positions of the lung parenchyma. It is also possible to determine the signal intensities $SI(\vec{x}_i)$ in step b.) by averaging the signal magnitudes of the MR images over certain regions of the lung parenchyma, in order to improve the reliability of the respiratory index $\alpha(\vec{x}_i)$. Thus, the MR images which are used to determine the signal intensities $SI(\vec{x}_i)$ represent the acquired MR data in image space (as opposed to the respective k-space data).

It is possible for the respiratory index $\alpha(\vec{x}_i)$ to represent a global measure of the function of the entire lung. In such a case, the region $\vec{x}_i$ denotes the entire lung parenchyma and the obtained respiratory index $\alpha(\vec{x}_i) = \alpha_{global}$ represents the function of the entire lung. More preferred, however, is an embodiment in which $\vec{x}_i$ denotes a position or region that only represents a part of the entire lung, more preferably a part of the right or the left lung, most preferably a part of one of the pulmonary lobes. In this case, the respiratory index $\alpha(\vec{x}_i)$ represents the function of only the respective part of the lung. In a particularly preferred embodiment, a plurality of respiratory indices $\alpha(\vec{x}_i)$ is determined, in order to assess the function of the lung parenchyma at a plurality of respective regions or positions $\vec{x}_i$ of the lung. Thus, in this case in which a plurality of respiratory indices $\alpha(\vec{x}_i)$ is determined, the index i runs from 1 to n, i.e. i=1 ... n, with n≥2, preferably n≥32, more preferably n≥64.

If steps a.), b.) and c.) are carried out for a plurality of regions or positions $\vec{x}_i$ of the lung parenchyma, then the determined respiratory indices $\alpha(\vec{x}_i)$ are preferably used to generate a two-dimensional or three-dimensional map reflecting the regional function of the lung. The map is preferably a color-coded map in which the color for each position or region $\vec{x}_i$ is dependent on the respiratory indices $\alpha(\vec{x}_i)$ as determined in step c.).

Preferably, the acquired MR images are spatially co-registered in the area of the lung parenchyma, advantageously in the area of the entire lung parenchyma, and, in step b.), the signal intensity $SI(\vec{x}_i)$ is determined for each of the spatially co-registered MR images. Thus, the positions or regions $\vec{x}_i$ in the plurality of co-registered MR images directly correspond to the same respective positions or regions $\vec{x}_i$ of the lung parenchyma. The spatial co-registration of the MR images is advantageously carried out for example by means of a deformable B-spline mass preserving image registration algorithm. Of course other registration algorithms or correlations analysis can be used.

Advantageously, the spatially co-registered MR images can be median-filtered, and, in step b.), the signal intensity $SI(\vec{x}_i)$ is determined for each of the spatially co-registered and median-filtered MR images. Median filtering is used to remove the overlying vascular structure from the MR images and get access to the parenchymal signal. Other filtering and post-processing methodology can also be advantageous.

A variety of possibilities are conceivable to estimate the change of the lung volume $V_L$ (or a part of the lung volume, e.g. a segment or lobe) between the different breathing positions in step a.), such as for example by means of a simple balloon. Spirometry measurements can also be applied for this purpose. In a preferred embodiment, however, the estimation of the lung volume $V_L$ for each of the different breathing positions is based on the acquired series of MR images or other imaging modalities (e.g. ultrasounds). For doing so, each of the acquired MR images can be segmented with respect to the lung parenchyma, such that, in step a.), the lung volume $V_L$ or a portion of it can be estimated for each of the different breathing positions based on the segmented MR images. An alternative method to estimate the change of the lung volume is based on a calculation of the determinant of the spatial Jacobian of the transformation field T, which links the positions of the tissue regions in the different images: $V(\vec{x}_i) = J(\vec{x}_i) = \det(\partial T/\partial \vec{x}_i)$ which can for example be calculated voxel-wise or in regions $\vec{x}_i$.

For the estimation of the lung volumes $V_L$, the acquired MR images are advantageously median-filtered prior to the segmentation, in order to facilitate the segmentation.

The series of MR images preferably represent the lung parenchyma at regularly distributed breathing positions from full expiration to maximum inspiration. In case the series of MR images only comprises two images, the images need to be at significantly different breathing position (phase). For example, one of these two images can be acquired at full expiration and the other at maximum inspiration. The determination of $\alpha(\vec{x}_i)$ in step c.) with two images only is straightforward: The difference between the signal intensities $SI(\vec{x}_i)$, divided by the difference of the respective lung volumes $V_L$, can be calculated.

Preferably, however, in order to obtain a more reliable result, the series of MR images comprises at least three images, more preferably at least five images, even more preferably at least nine images, and most preferably at least 13 images. In this case, in step c.), the at least one respiratory index $\alpha(\vec{x}_i)$ is advantageously determined by means of a linear fit. Otherwise, the respiratory indices $\alpha(\vec{x}_i)$ can be calculated between each two images, thus calculating $\alpha(\vec{x}_i, I_{p1}, I_{p2})$, where $I_{p1}$ and $I_{p2}$ indicate two images at different breathing positions.

In order to enable a more precise and in particular quantitative determination of the at least one respiratory index $\alpha(\vec{x}_i)$ in step c.), a multiplication with the factor $$\frac{1}{1 - SNR^{-1}}$$

is further carried out, in order to yield the formula $$\alpha(\vec{x}_i) = -\frac{1}{1 - SNR^{-1}} \cdot \frac{d(\log(SI(\vec{x}_i)))}{d(\log(V_L))},$$

wherein SNR denotes an estimated signal-to-noise ratio $SI(\vec{x}_i)/\eta$ in which $\eta$ represents the estimated intensity of noise in the MR images in the at least one region or position $\vec{x}_i$.

The equation of the adapted sponge model, $SI(V_L) = \Lambda * V_L^{-\alpha} + \eta$, can be rewritten on a logarithmic scale to yield $$\log(SI) = \log\left(\Lambda * V_L^{-\alpha}\left(1 + \frac{\eta}{\Lambda * V_L^{-\alpha}}\right)\right),$$

from which the respiratory index α can be estimated as follows:

$$\frac{\partial SI}{\partial (\log(V_L))} = -\alpha \cdot \frac{\Lambda \cdot V_L^{-\alpha}}{\Lambda \cdot V_L^{-\alpha} + \eta} = -\alpha \cdot \left(1 - \frac{\eta}{\Lambda \cdot V_L^{-\alpha} + \eta}\right) = -\alpha \cdot \left(1 - \frac{\eta}{SI}\right)$$

$$\Rightarrow \alpha := -\frac{1}{1 - \frac{\eta}{SI}} \cdot \frac{d(\log(SI))}{d(\log(V_L))} = -\frac{1}{1 - SNR^{-1}} \cdot \frac{d(\log(SI))}{d(\log(V_L))}$$

Generally, the noise η might vary for each patient, for each MRI scanner, and for each acquisition, and becomes prominent particularly in pulmonary MRI. This is caused by the physical characteristic of the lung, e.g. low and variable density together with susceptibility effects, which cause both a low detectable SI and strong SI variations amongst the pulmonary tissue (e.g. dorsal/ventral part, dependent/non-dependent, perfused/non-perfused). As a result, the factor $$\frac{1}{1 - SNR^{-1}}$$

plays a crucial role in determining the precise value of α. By applying this factor, not only a qualitative assessment, but a quantitative examination of the regional lung function becomes possible, which in turn enables follow-up studies, e.g. of obstructive pulmonary disease patients.

Additionally, a magnetic resonance imaging (MRI) system is provided which is configured to carry out the method as indicated. Usually, such a MRI system comprises at least:
- a main magnet for generating a main, particularly static magnetic field $B_0$ at a location of a sample, i.e. a human or an animal, to be imaged, in order to at least partly align nuclear spins of the sample;
- an excitation module for applying a sequence of radio frequency (RF) pulses to the sample, in order to repeatedly excite the nuclear spins of the sample;
- a gradient module for generating temporary magnetic gradient fields at a location of the sample;
- an acquisition module, in particular an image acquisition module, for acquiring the magnetic resonance (MR) signals produced by excited nuclear spins of the sample; and
- a control module configured for controlling the excitation module, the gradient module and the acquisition module such, that a series of MR images of the lung parenchyma of a human or an animal can be acquired at different breathing positions.

Furthermore, the MRI system comprises an analysis module being configured for determining a signal intensity $SI(\vec{x}_i)$ in at least one same region or position $\vec{x}_i$ of the lung parenchyma for each of the MR images and being configured for determining at least one respiratory index $\alpha(\vec{x}_i)$ according to the formula $$\alpha(\vec{x}_i) = -\frac{d(\log(SI(\vec{x}_i)))}{d(\log(V_L))},$$

wherein $V_L$ denotes a lung volume for each of the different breathing positions.

It is preferred, that the magnetic field $B_0$ generated by the main magnet is essentially uniform at least in the region of the sample. The magnitude of the magnetic field generated by the main magnet is preferably larger than 0.5 Tesla, more preferably larger than 1 Tesla, even more preferably larger than 2 Tesla and most preferably larger than 5 Tesla. With a stronger magnetic field, a better signal-to-noise ratio can be achieved, but imaging artifacts are also more pronounced.

The MRI system preferably also comprises an image reconstruction module for reconstructing images based on the acquired k-space data.

Preferably, the analysis module is further configured for estimating change of the lung volume $V_L$ (or a portion of it) between the different breathing positions based on the MR images. For this purpose, the analysis module can particularly be configured to median filter and segment the MR images, wherein the segmentation process is advantageously assisted by user interaction.

In a particularly preferred embodiment, the analysis module is also configured for carrying out a multiplication with the factor $$\frac{1}{1 - SNR^{-1}}$$

in the determination of the at least one respiratory index $\alpha(\vec{x}_i)$, in order to yield the formula $$\alpha(\vec{x}_i) = -\frac{1}{1 - SNR^{-1}} \cdot \frac{d(\log(SI(\vec{x}_i)))}{d(\log(V_L))},$$

wherein SNR denotes an estimated signal-to-noise ratio $SI(\vec{x}_i)/\eta$ in which η represents the estimated intensity of noise in the MR images in the at least one region or position $\vec{x}_i$.

Furthermore, a computer program, preferably stored on a storage device readable by a computer, is provided comprising executable instructions to carry out the method as indicated when being executed e.g. in a processor of a computer, in particular in a processor of a MRI system or in a processer being connected with a MRI system. The computer program is usually realized as a computer program code element which comprises computer-implemented instructions to cause a processor to carry out a particular method. It can be provided in any suitable form, including source code or object code. In particular, it can be stored on a computer-readable medium or embodied in a data stream. The data stream may be accessible through a network such as the Internet.

Thus, the computer program serves for the assessment of the lung parenchyma in a human or an animal by means of a series of magnetic resonance (MR) images of the lung parenchyma acquired at different breathing positions in the same human or animal. The computer program comprises at least executable instructions to:

b.) determine a signal intensity $SI(\vec{x}_i)$ in at least one same region or position $\vec{x}_i$ of the lung parenchyma for each of the MR images; and c.) determine at least one respiratory index $\alpha(\vec{x}_i)$ according to the formula $$\alpha(\vec{x}_i) = -\frac{d(\log(SI(\vec{x}_i)))}{d(\log(V_L))},$$

wherein $V_L$ denotes a lung volume for each of the different breathing positions.

The computer program can also comprise executable instructions for controlling a magnetic resonance imaging (MRI) system as described. In this case, the computer program also comprises executable instructions to employ a MR imaging sequence in an additional step a0.), such as a 3D ufSSFP imaging sequence, on the MRI system in such a way, that a series of MR images of the lung parenchyma of a human or an animal is acquired at different breathing positions.

The computer program advantageously additionally comprises executable instructions to estimate, in an additional step a.), the change of the lung volume $V_L$ between the different breathing positions based on the MR images, in particular according to one of the methods as set out above in respect to this purpose.

The executable instructions of the computer program to determine at least one respiratory index $\alpha(\vec{x}_i)$ in step c.) preferably also comprise a multiplication with the factor $$\frac{1}{1 - SNR^{-1}},$$

in order to yield the formula $$\alpha(\vec{x}_i) = -\frac{1}{1 - SNR^{-1}} \cdot \frac{d(\log(SI(\vec{x}_i)))}{d(\log(V_L))},$$

wherein SNR denotes an estimated signal-to-noise ratio $SI(\vec{x}_i)/\eta$ in which $\eta$ represents the estimated intensity of noise in the MR images in the at least one region or position $\vec{x}_i$.

SHORT DESCRIPTION OF THE FIGURES

Preferred embodiments of the invention are described in the following with reference to the drawings, which only serve for illustration purposes, but have no limiting effects. In the drawings it is shown.

DESCRIPTION OF PREFERRED EMBODIMENTS

Figure 1:
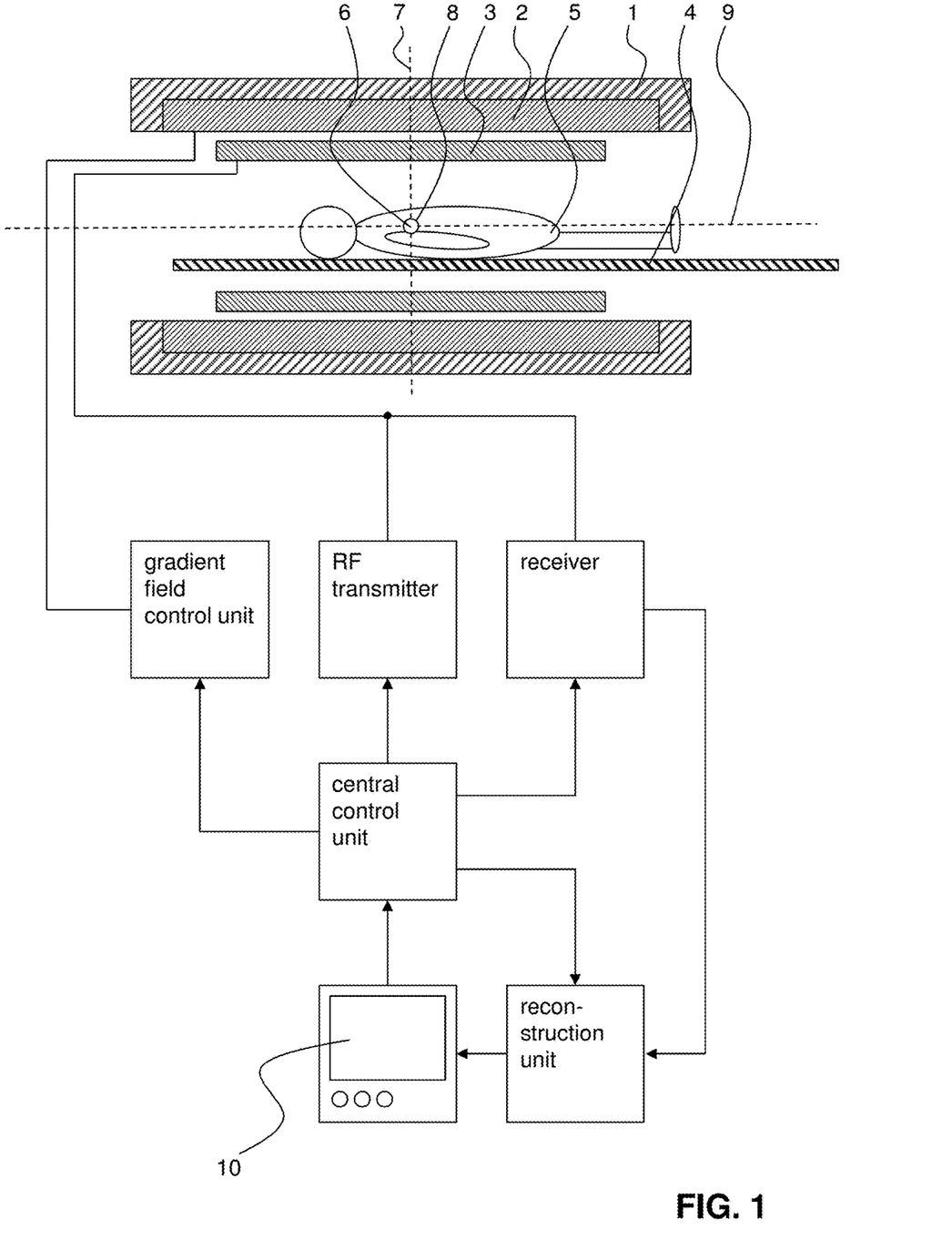
FIG. 1 a schematic illustration of a MRI system for carrying out the inventive method according to an inventive embodiment.
Figure 2:
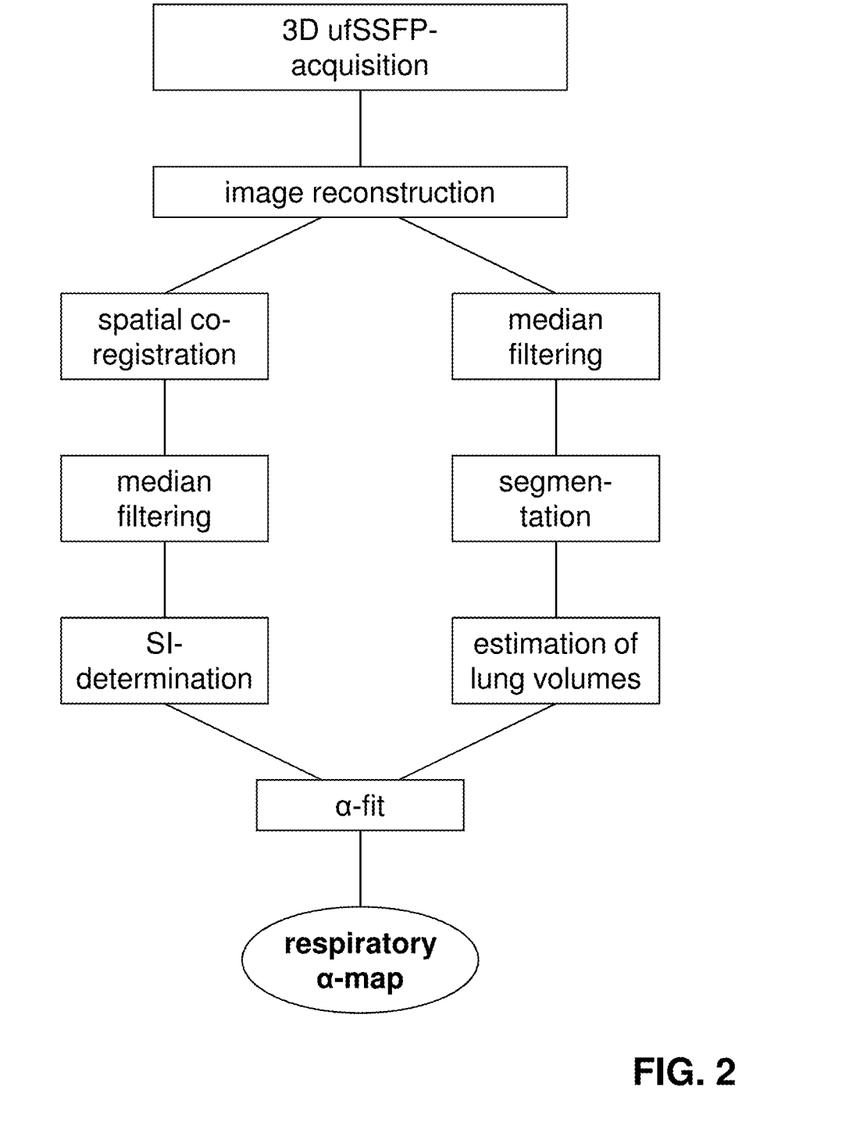
FIG. 2 a flow chart illustrating a preferred example for carrying out the inventive method.

In FIG. 1, an exemplary MRI system is shown which serves to carry out the inventive method for the assessment of the lung parenchyma in a human or an animal. A flow chart illustrating an example of an inventive method is shown in FIG. 2.

The MRI system comprises a main magnet 1 for producing a main magnetic field $B_0$. The main magnet 1 usually has the essential shape of a hollow cylinder with a horizontal bore. Inside the bore of the main magnet 1 a magnetic field is present, which is essentially uniform at least in the region of the isocenter 6 of the main magnet 1. The main magnet 1 serves to at least partly align the nuclear spins of a sample 5 arranged in the bore. The sample 5 is represented by a human or an animal. Of course, the magnet 1 does not necessarily be cylinder-shaped, but could for example also be C-shaped.

The human or animal patient is arranged in such a way on a moving table 4 in the bore of the main magnet 1, that the lung, the function of which is being assessed, is arranged in the region of the isocenter 6 of the magnet 1. In order to avoid motion artefacts, the patient is instructed to not move during data acquisition.

The main magnet 1 has a z-axis 9 which coincides with the central longitudinal axis defined by the cylindrical shape of the magnet 1. Together with a x-axis 7 and a y-axis 8, which each extend in mutually perpendicular directions with respect to the z-axis 9, the z-axis 9 defines a Cartesian coordinate system of the MRI system, having its origin at the isocenter of the magnet 1.

In order to produce a magnetic field which linearly varies in the direction of the x-axis 7, the y-axis 8 and/or the z-axis 9, the MRI-system comprises a gradient system 2 including several coils for producing these varying magnetic fields. A radiofrequency (RF) coil 3 is provided for generating a transmit field $B_1$, in order to repetitively excite the nuclear spins of the sample 5.

As illustrated in FIG. 2, the sample 5 is subjected to a 3D ultra-fast balanced SSFP (ufSSFP) sequence. The 3D ufSSFP sequence is initiated by an operator by means of a user interface 10, which sends the respective instructions to a central control unit of the MRI system (FIG. 1). The central control unit controls a gradient field control unit being connected with the gradient system 2 as well as a RF transmitter and a receiver both being connected with the RF coil 3. The gradient system 2 and the gradient field control unit together constitute a gradient module of the MRI system. The central control unit controls the gradient field control unit, the RF transmitter and the receiver such, that a 3D ufSSFP imaging sequence is employed on the MRI system, which allows the acquisition of MR images of the entire lung parenchyma at different breathing positions. The patient is instructed to hold his breath during the data acquisition accordingly. Of course it is also possible to acquire the required MR images in free breathing.

The receiver, which constitutes an acquisition module together with the RF coil 3, is connected with a reconstruction unit, in which the acquired MR signals are reconstructed to form the respective MR image data sets. After completed image acquisition, these image data sets, which are still spatial spectral image data sets in k-space are transferred to image space by means of an (inverse) Fourier transformation carried out by the reconstruction unit (image reconstruction in FIG. 2). In order to account for the specific imaging parameters applied during image acquisition, the reconstruction unit is connected with the central control unit. The reconstructed MR images are then sent to the user interface 10.

In a concrete measurement, all datasets, i.e. MR images, were acquired with a 1.5 T clinical whole-body MR-scanner (Siemens Healthcare, Erlangen, Germany) using a 12-channel thorax and a 24-channel spine coil receive-array and the body coil as the transmitter. Images of human patients were acquired in breath-hold and in supine position using a 3D ufSSFP protocol, with the following imaging parameters: TE/TR=0.47/1.19 ms, flip angle 23°, RF pulse length=80 µs, 1563 Hz/pixel bandwidth, field-of-view=$450^2 \times 200$-250 mm$^3$, two averages, isotropic resolution=3.5 mm$^3$, reconstruction matrix=$128^2 \times 72$-80, parallel imaging with a GRAPPA factor 2, phase oversampling 50%, for a total acquisition time=11-17 s. Predefined default shim settings (tune MR up) were used. Five to 14 scans, i.e. MR images, were recorded at different breathing positions from forced expiration to forced inspiration.

In the user interface 10, which also represents an analysis module and is usually realized by a customary personal computer having a processor, the acquired and reconstructed MR images are further processed, in order to obtain respiratory α-maps of the lung parenchyma.

In order to obtain the respiratory α-maps, the signal intensities $SI(\vec{x}_i)$ of a plurality of positions or regions $\vec{x}_i$ of the lung parenchyma need to be determined for the different breathing positions. In parallel to the determination of the signal intensities, the lung volumes $V_L$ are estimated for each of the different breathing positions.

As shown in FIG. 2, for the determination of the signal intensities $SI(\vec{x}_i)$, in a first step the reconstructed MR images are spatially co-registered in the area of the lung parenchyma. The spatial co-registration can be achieved using a 3D deformable B-spline mass preserving image registration algorithm. This can for example be done using the open source software elastix (elastix version 4.7, University Medical Center Utrecht, The Netherlands). For registration, a scan with a mean value of the lung volume can be chosen as fixed dataset (baseline) and the other, so-called 'moving' datasets can be co-registered.

The co-registered MR images are then median filtered to remove the overlying vascular structure, but preserving the underlying pulmonary signal variation. With the data sets acquired with the MR imaging parameters as set out above, it is proposed to use a filter kernel size of 5×5×5 voxels for median filtering.

From the spatially co-registered and median filtered images, the signal intensities $SI(\vec{x}_i)$ can then be determined in each of the MR images acquired at different breathing positions for a plurality of positions or regions $\vec{x}_i$ in a straightforward way.

The estimation of the lung volumes $V_L$ in the different breathing positions is preferably based on the same acquired MR images as the determination of the signal intensities $SI(\vec{x}_i)$. As shown in FIG. 2, in a first step the reconstructed MR images are median filtered to remove the overlying vascular structure, but preserving the underlying pulmonary signal variation. As in the determination of the signal intensities $SI(\vec{x}_i)$, it is proposed to use a filter kernel size of 5×5×5 voxels for median filtering the data sets acquired with the MR imaging parameters as set out above.

The lung volumes are then segmented in each of the median filtered MR images. For the segmentation, it is proposed to use a 2D or 3D fast-marching algorithm and to verify the consistency of the segmentation slice-by-slice and in between datasets by a trained observer. If needed, the regions-of-interest (ROI) can be corrected manually.

Based on the segmentation, the volumes $V_L$ of the lung in each acquisition can be calculated by the analysis module.

Finally, the respiratory indices $\alpha(\vec{x}_i)$ are determined by the analysis module according to the formula $$\alpha(\vec{x}_i) = -\frac{1}{1 - SNR^{-1}} \cdot \frac{d(\log(SI(\vec{x}_i)))}{d(\log(V_L))},$$

SNR denotes an estimated signal-to-noise ratio $SI(\vec{x}_i)/\eta$ in which η represents the estimated intensity of noise in the MR images in the regions or positions $\vec{x}_i$. By applying the optional factor $$\frac{1}{1 - SNR^{-1}},$$

more reliable α-values can be obtained, which allow for a quantitative assessment of regional lung function independently of the SNR.

The noise η is preferably determined in the MR images by a ROI analysis, e.g. a ROI placed in the air and away from the body. In this case, the same SNR is assumed for all MR images and for all regions or positions $\vec{x}_i$. Alternatively, the same MR sequence as used for the 3D ufSSFP acquisition can be run with flip angles of 0°, in order to assess the noise η in the images.

The determination of the respiratory indices $\alpha(\vec{x}_i)$ is carried out by means of a linear fit in the double logarithmic scale of $SI(\vec{x}_i)$ and $V_L$ (see FIG. 4, as explained further below). The obtained respiratory indices $\alpha(\vec{x}_i)$ are then graphically represented on a respiratory α-map, in which the values of the respiratory indices $\alpha(\vec{x}_i)$ are preferably color-coded and overlaid on a respective 3D ufSSFP morphological image.

Figure 3A:
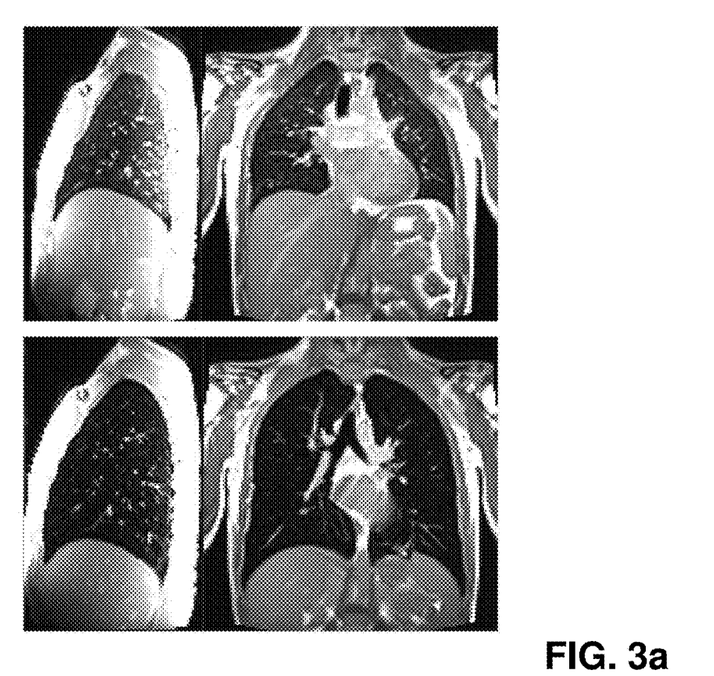
FIG. 3a exemplary sagittal and coronal 3D ufSSFP chest images illustrating end-expiration (top) and full inspiration (bottom)
Figure 3B:
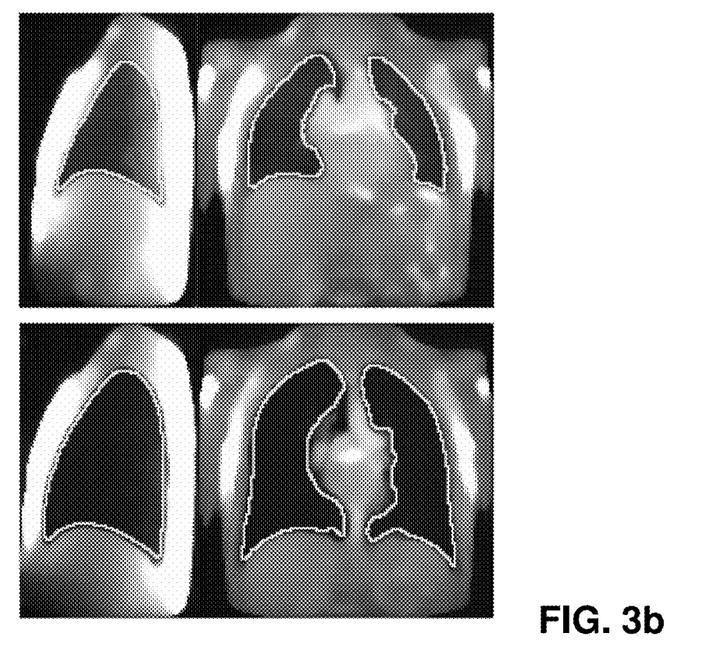
FIG. 3b the MR images of FIG. 3a after median-filtering and with segmentation (white outline) used for estimation of parenchymal signal intensity and lung volume.

Exemplary native 3D ufSSFP images obtained in a healthy volunteer are shown in FIG. 3*a* for two different inspiratory volumes (i.e. end-expiration with 1.8 L in the top row and full inspiration with 4.6 L in the bottom row). As a result of the very short TR, no banding artefacts are visible and airways are well visualized in the native images. The difference in signal levels in the lung parenchyma for the two lung volumes are clearly noticeable; especially in the dependent (dorsal) part of the lung. Median filtering, as shown in FIG. 3b, is used to remove the overlying vascular structure, but preserving the underlying pulmonary signal variation (24). The segmentation of the lung is shown in FIG. 3b by means of the white outline.

Figure 4:
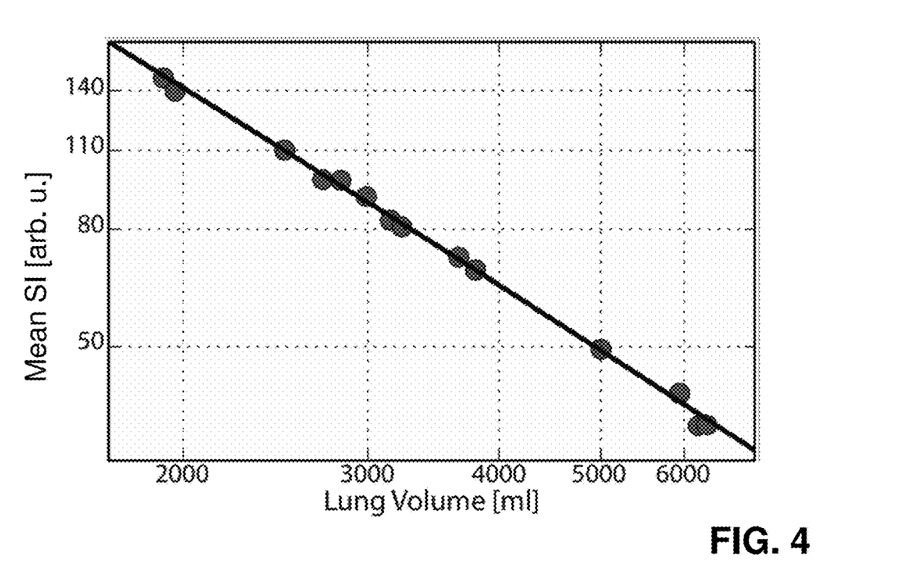
FIG. 4 the mean signal intensity of the parenchyma (dots) as a function of the lung volume in double logarithmic scale as well as a fit of the adapted sponge model (black line) yielding $\alpha_{global}=1.16\pm0.02$.

The observed mean parenchymal signal intensity variation (over the whole lung; see white outlines in FIG. 3b for definition of the region-of-interest) is shown in FIG. 4 as a function of lung volumes $V_L$ for the MR images acquired with the parameters as set out above. The overall SI variation of the lung parenchyma is as low as 36 [a.u.] in forced inspiration ($V_L$=6.31 L) and increased about 4-times, up to 147 [a.u.], in forced expiration ($V_L$=1.92 L). In comparison to the signal intensity emanating from the lung parenchyma, a low noise level of about 5±2 [a.u.] is measured in air justifying the assumption of $\eta \ll \Lambda^* V_L^{-\alpha}$.

Overall, the signal variation as shown in FIG. 4 almost perfectly follows the adapted sponge model. A linear fit of the adapted sponge model in the double logarithmic scale yields $\alpha_{global}$=1.16±0.02 in combination with a SI scaling factor $\Lambda$=317±7 [a.u.]. The small residual deviations of the experimental data from the linear fit in the double logarithmic scale corroborate the overall independency of the respiratory index from the breathing phase. Moreover, a respiratory index $\alpha_{global}$ deviating from 1 indicates a change in lung mass during breathing and that the dry sponge model ($\alpha$=1) is not accurate to describe the lung SI modulations.

Figure 5A:
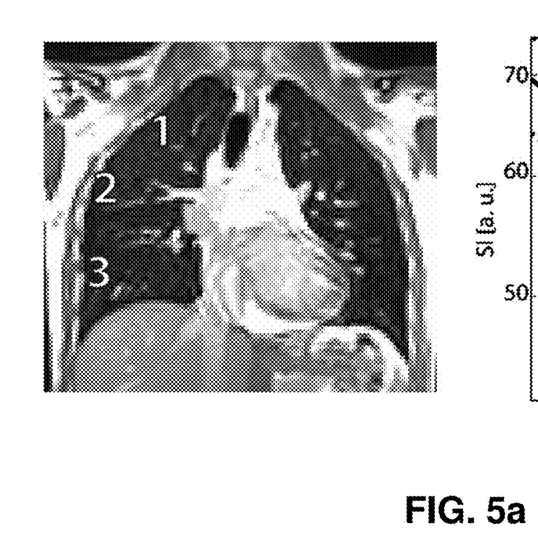
FIG. 5a another exemplary 3D ufSSFP coronal view with three region-of-interests 1, 2 and 3 being indicated by respective numbers.

Another exemplarily coronal view of a 3D ufSSFP acquisition in a healthy volunteer is shown in FIG. 5a. Four other images which are not shown were acquired at different breathing positions. From this image acquisition, a global respiratory index $\alpha_{global}$=1.04±0.03 is recovered.

Figure 5B:
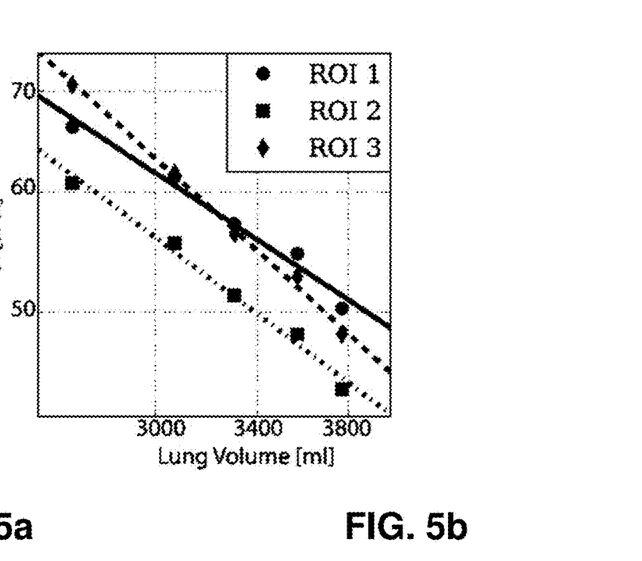
FIG. 5b the local parenchymal signal (averaged over 4×4×4 voxels) as a function of the lung volume in double logarithmic scale for the three region-of-interests indicated in FIG. 5a, yielding $\alpha_1=0.81\pm0.07$, $\alpha_2=0.93\pm0.07$ and $\alpha_3=1.13\pm0.05$.

For three different regions-of-interests (4×4×4 voxels), the mean SI, as observed in the five datasets after image co-registration, is shown in FIG. 5b. Local respiratory index values $\alpha_{local}$ of 0.88±0.07, 0.93±0.07 and 1.13±0.05 are found with an $R^2$ exceeding 0.976, indicating appropriate description of the data by the adapted sponge model after image registration.

Figure 6:
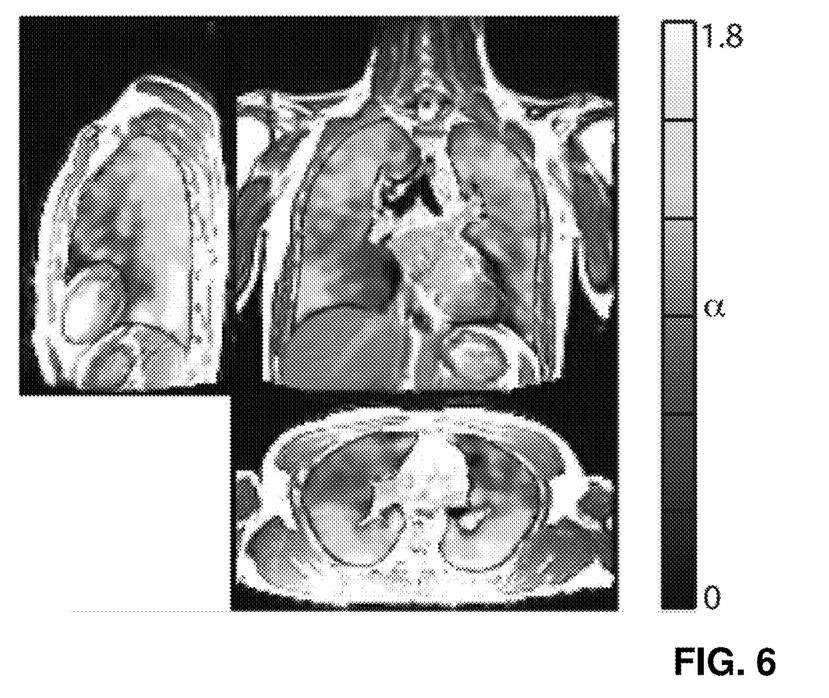
FIG. 6 exemplary 3D respiratory $\alpha$-maps overlaid on 3D ufSSFP morphological images in sagittal, coronal and transverse orientation for a healthy volunteer.

Respiratory index maps for a healthy male volunteer are shown in FIG. 6 for representative slices in coronal, sagittal, and axial orientations. Generally, a homogenous respiratory index is observed on isogravitational planes, whereas the respiratory index values almost double in the caudal part ($\alpha \approx 1.4$) in comparison to ventral part ($\alpha \approx 0.7$).

Figure 7A:
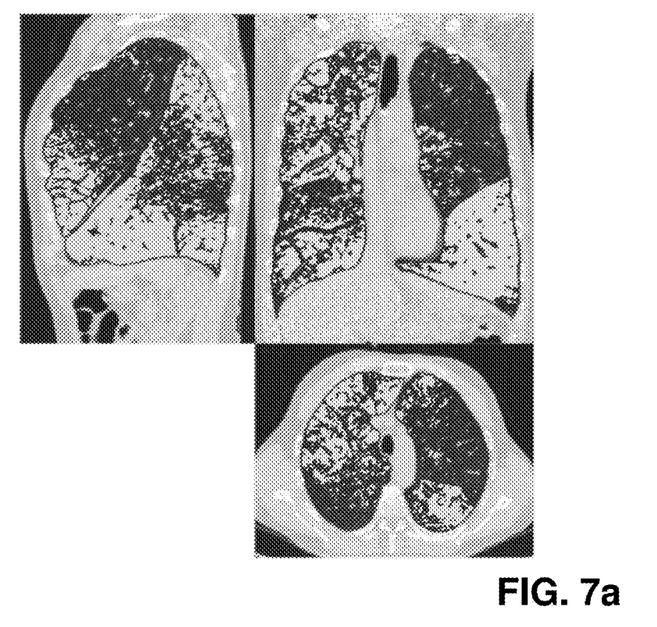
FIG. 7a exemplary CT emphysema maps in sagittal, coronal and transverse orientation for a patient suffering under chronic obstructive pulmonary disease (COPD)
Figure 7B:
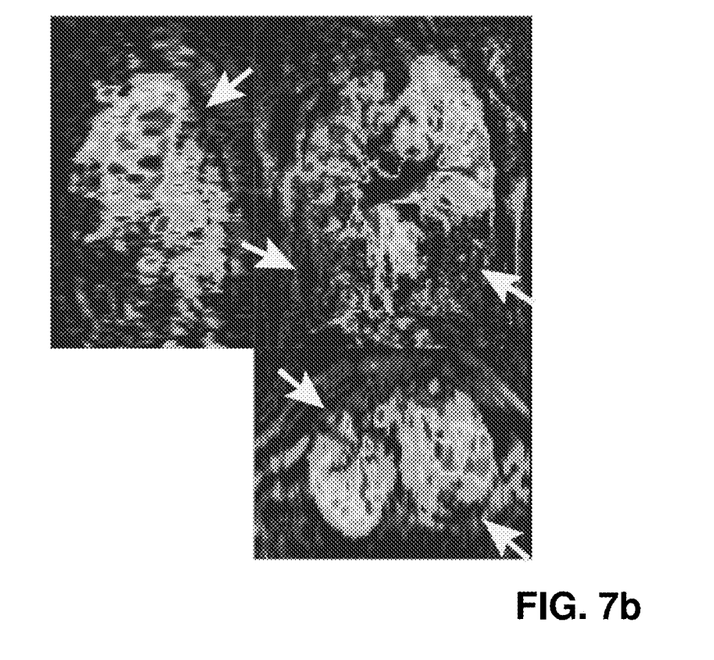
FIG. 7b images acquired by means of dynamic contrast-enhanced MRI (DCE-MRI) in the same views and in the same patient as in FIG. 7a, with arrows indicating functional defects.
Figure 7C:
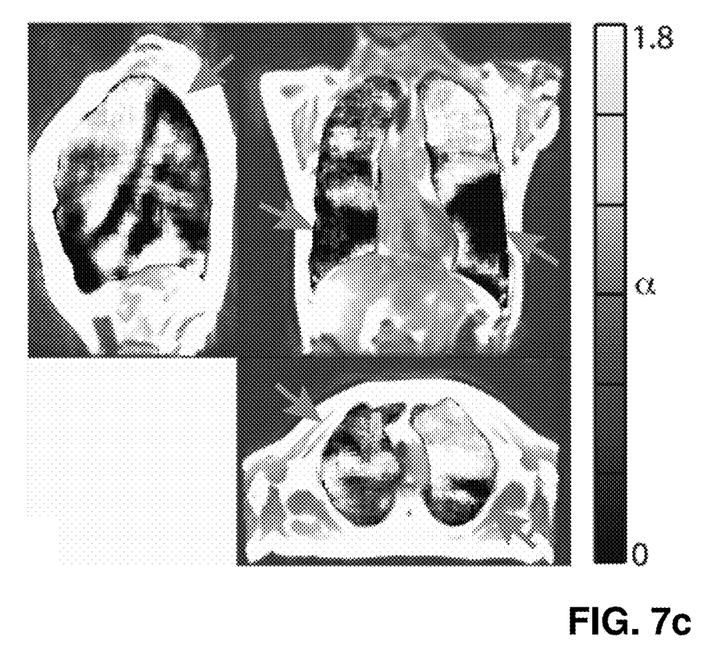
FIG. 7c respiratory index maps obtained by means of the inventive method in the same views and in the same patient as in FIG. 7a, with arrows indicating functional defects.

Respiratory index maps obtained in a patient suffering under chronic obstructive pulmonary disease (COPD) are shown in FIG. 7c and are compared to CT (FIG. 7a) and DCE MRI (FIG. 7b). CT emphysema maps reveal impairments for the COPD patient: There are localized large emphysematous regions. Similar abnormalities are seen on DCE perfusion images (arrows in FIG. 7b). Overall, structural emphysematous tissue destructions and perfusion defects visually correlate with the location of conspicuous functional impairment indicated on the respiratory maps (e.g. $\alpha_{local}$<0.3; arrows in FIG. 7c). FIGS. 7a, b, c demonstrate the feasibility of respiratory index mapping by means of the inventive method in the clinical setting.

REFERENCE NUMERALS

| 1 | Main magnet |
| 2 | Gradient system |
| 3 | RF coil |
| 4 | Moving table |
| 5 | Patient |
| 6 | Isocenter |
| 7 | X-axis |
| 8 | Y-axis |
| 9 | Z-axis |
| 10 | User interface |

The invention claimed is:

1. A method for the assessment of the lung parenchyma in a human or an animal using a series of magnetic resonance (MR) images of the lung parenchyma acquired at different breathing positions in the same human or animal, comprising the following steps:
   a.) estimating a change of a lung volume $V_L$ between the different breathing positions;
   b.) determining a signal intensity $SI(\vec{x}_i)$ in at least one region or position $\vec{x}_i$ of the lung parenchyma for each image of the series of MR images, the at least one region or position $\vec{x}_i$ of the lung parenchyma being the same for each image of the series of MR images;
   c.) determining at least one respiratory index $\alpha(\vec{x}_i)$ according to the formula $$\alpha(\vec{x}_i) = -\frac{d(\log(SI(\vec{x}_i)))}{d(\log(V_L))};$$

and
   d.) assessing the function of the lung parenchyma at a plurality of respective regions or positions $\vec{x}_i$ of the lung based on the determined at least one respiratory index $\alpha(\vec{x}_i)$.

2. The method as claimed in claim 1,
   wherein the images of the acquired series of MR images are spatially co-registered in the area of the lung parenchyma, and
   wherein, in step b.), the signal intensity $SI(\vec{x}_i)$ is determined for each of the spatially co-registered images of the series of MR images.

3. The method as claimed in claim 2, wherein the spatial co-registration of the images of the series of MR images is carried out by means of a deformable B-spline mass preserving image registration algorithm.

4. The method as claimed in claim 2,
   wherein the spatially co-registered images of the series of MR images are median-filtered, and wherein, in step b.), the signal intensity $SI(\vec{x}_i)$ is determined for each of the spatially co-registered and median-filtered images of the series of MR images.

5. The method as claimed in claim 1,
   wherein the estimation of the lung volume $V_L$ for each of the different breathing positions is based on the acquired series of MR images.

6. The method as claimed in claim 5,
   wherein each image of the acquired series of MR images is segmented with respect to the lung parenchyma, and wherein, in step a.), the lung volume $V_L$ is estimated for each of the different breathing positions based on the segmented images of the series of MR images.

7. The method as claimed in claim 6, wherein the images of the acquired series of MR images are median-filtered prior to the segmentation.

8. The method as claimed in claim 1, wherein the series of MR images comprises at least three images, and wherein, in step c.), the at least one respiratory index $\alpha(\vec{x}_i)$ is determined by means of a linear fit.

9. The method as claimed in claim 1, wherein steps b.) and c.) are carried out for a plurality of regions or positions $\vec{x}_i$ of the lung parenchyma.

10. The method as claimed in claim 9, wherein the determined respiratory indices $\alpha(\vec{x}_i)$ are used to generate a two-dimensional or three-dimensional map.

11. The method as claimed in claim 1, wherein, in the determination of the at least one respiratory index $\alpha(\vec{x}_i)$ in step c.), a multiplication with the factor $$\frac{1}{1 - SNR^{-1}}$$

is miner carried out, in order to yield the formula $$\alpha(\vec{x}_i) = -\frac{1}{1 - SNR^{-1}} \cdot \frac{d(\log(SI(\vec{x}_i)))}{d(\log(V_L))},$$

wherein SNR denotes an estimated signal-to-noise ratio $SI(\vec{x}_i)/\eta$ in which $\eta$ represents the estimated intensity of noise in the series of MR images in the at least one region or position $\vec{x}_i$.

12. The method as claimed in claim 1, additionally comprising, before step b.), the step that
a series of MR images of the lung parenchyma is acquired at different breathing positions by means of a MR imaging system.

13. The method as claimed in claim 12, wherein the series of MR images is acquired by means of a balanced steady state free precession (SSFP) imaging sequence.

14. A computer program product for the assessment of the lung parenchyma in a human or an animal, the computer program product comprising a non-transitory computer-readable medium comprising executable instructions to cause a processor of a computer to carry out the following steps by means of a series of magnetic resonance (MR) images of the lung parenchyma acquired at different breathing positions in the same human or animal:

i.) determining a signal intensity $SI(\vec{x}_i)$ in at least one region or position $\vec{x}_i$ of the lung parenchyma for each image of the series of MR images, the at least one region or position $\vec{x}_i$ of the lung parenchyma being the same for each image of the series of MR images; and ii.) determining at least one respiratory index $\alpha(\vec{x}_i)$ according to the formula $$\alpha(\vec{x}_i) = -\frac{d(\log(SI(\vec{x}_i)))}{d(\log(V_L))},$$

wherein $V_L$ denotes a lung volume for each of the different breathing positions.

15. The computer program product as claimed in claim 14, additionally comprising executable instructions to:
acquire, before step i.), the series of MR images of the lung parenchyma at different breathing positions by means of a MR imaging system and to
estimate, before step ii.), a change of the lung volume $V_L$ between the different breathing positions based on the acquired series of MR images.

16. The computer program product as claimed in claim 14, wherein, in the determination of the at least one respiratory index $\alpha(\vec{x}_i)$ in step ii.), a multiplication with the factor $$\frac{1}{1 - SNR^{-1}}$$

is further carried out, in order to yield the formula $$\alpha(\vec{x}_i) = -\frac{1}{1 - SNR^{-1}} \cdot \frac{d(\log(SI(\vec{x}_i)))}{d(\log(V_L))},$$

wherein SNR denotes an estimated signal-to-noise ratio $SI(\vec{x}_i)/\eta$ in which $\eta$ represents the estimated intensity of noise in the series of MR images in the at least one region or position $\vec{x}_i$.

17. A magnetic resonance imaging (MRI) system comprising:
a main magnet for generating a main magnetic field at a location of a sample to be imaged, in order to at least partly align nuclear spins of the sample;
an excitation module for applying radio frequency (RF) pulses to the sample, in order to repeatedly excite the nuclear spins of the sample;
a gradient module for generating temporary magnetic gradient fields at a location of the sample;
an acquisition module for acquiring the magnetic resonance signals produced by excited nuclear spins of the sample;
a control module configured for controlling the excitation module, the gradient module and the acquisition module such, that a series of MR images of the lung parenchyma of a human or an animal can be acquired at different breathing positions; and
an analysis module being configured for determining a signal intensity $SI(\vec{x}_i)$ in at least one region or position $\vec{x}_i$ of the lung parenchyma for each image of the series of MR images, the at least one region or position $\vec{x}_i$ of the lung parenchyma being the same for each image of the series of MR images, and being configured for determining at least one respiratory index $\alpha(\vec{x}_i)$ according to the formula $$\alpha(\vec{x}_i) = -\frac{d(\log(SI(\vec{x}_i)))}{d(\log(V_L))},$$

wherein $V_L$ denotes a lung volume for each of the different breathing positions.

18. The MRI system as claimed in claim 17, the analysis module further being configured for estimating a change of the lung volume $V_L$ between the different breathing positions based on the series of MR images.

19. The MRI system as claimed in claim 17,
wherein the analysis module is further configured for carrying out a multiplication with the factor $$\frac{1}{1-SNR^{-1}}$$

in the determination of the at least one respiratory index $\alpha(\vec{x}_i)$, in order to yield the formula $$\alpha(\vec{x}_i) = -\frac{1}{1-SNR^{-1}} \cdot \frac{d(\log(SI(\vec{x}_i)))}{d(\log(V_L))},$$

wherein SNR denotes an estimated signal-to-noise ratio $SI(\vec{x}_i)/\eta$ in which $\eta$ represents the estimated intensity of noise in the series of MR images in the at least one region or position $\vec{x}_i$.

* * * * *